United States Patent [19]

Matsuda et al.

[11] Patent Number: 4,959,976
[45] Date of Patent: Oct. 2, 1990

[54] REFRIGERATOR, DRY AIR GENERATING DEVICE FOR THE SAME, AND METHOD FOR OPERATING THE DEVICE

[75] Inventors: Shinichi Matsuda, Kanagawa; Yoshio Saito, Saitama; Hideo Ishizaka, Kanagawa, all of Japan

[73] Assignee: Fuji Photo Film Co., Ltd., Kanagawa, Japan

[21] Appl. No.: 444,906

[22] Filed: Dec. 4, 1989

[30] Foreign Application Priority Data

Dec. 7, 1988 [JP] Japan .................................. 63-309385
Dec. 7, 1988 [JP] Japan .................................. 63-309388

[51] Int. Cl.$^5$ ...................... F25D 23/12; G01N 31/00
[52] U.S. Cl. .......................................... 62/271; 34/153; 422/66
[58] Field of Search .................... 34/153, 155; 422/66; 436/44; 62/271

[56] References Cited

U.S. PATENT DOCUMENTS

| | | | |
|---|---|---|---|
| 2,504,703 | 4/1950 | Kuljian | 34/153 X |
| 3,526,480 | 9/1970 | Findl et al. | 422/66 |
| 3,675,488 | 7/1972 | Viktora et al. | 422/66 X |
| 4,077,137 | 3/1978 | Edgington et al. | 34/155 X |
| 4,293,212 | 10/1981 | Siryj et al. | 34/155 X |

FOREIGN PATENT DOCUMENTS

53-21677 7/1978 Japan .
55-164356 12/1980 Japan .
56-77746 6/1981 Japan .

*Primary Examiner*—William E. Tapolcal
*Attorney, Agent, or Firm*—Sughrue, Mion, Zinn, Macpeak & Seas

[57] ABSTRACT

A refrigerator comprises a cassette accommodating section which is enclosed by a wall, kept at a low temperature, and capable of accommodating a film feed cassette in such a way that it can be released therefrom. The film feed cassette houses therein a long test film containing a reagent which will react with a liquid sample and give rise to a change in optical density. The film feed cassette has a film outlet through which the long test film is fed out. The refrigerator has a film outlet which is formed in the wall at a position corresponding to the position of the film outlet of the film feed cassette and through which the long test film is pulled out. An air stream jetting system jets dry air to the surface of the portion of the long test film positioned between the film outlet of the film feed cassette and the film outlet of the refrigerator. The air stream jetting system comprises a device wherein two air drying chambers are alternately operated, which allows dry air to be generated approximately continuously, and wet air does not enter a dry air feed-out path even for an instant.

7 Claims, 6 Drawing Sheets

REFRIGERATOR, DRY AIR GENERATING DEVICE FOR THE SAME, AND METHOD FOR OPERATING THE DEVICE

BACKGROUND OF THE INVENTION

1. Field of the Invention

This invention relates to a refrigerator used in a biochemical analysis apparatus which is capable of accommodating a film feed cassette in such a way that the cassette can be released therefrom. The film feed cassette houses a long test film which has not yet been used in an analysis of a liquid sample. This invention also relates to a dry air generating device which continuously generates dry air and which is suitable for use with the refrigerator, and a method for operating the dry air generating device.

2. Description of the Prior Art

Qualitative or quantitative analyses of specific chemical constituents in liquid samples are conducted for various industrial purposes. Particularly, it is very important in biochemical and clinical fields to be able to quantitatively analyze certain chemical or physical constituents in body fluids, such as blood or urine.

Recently, as disclosed in, for example, Japanese Patent Publication No. 53(1978)-21677 and Japanese Unexamined Patent Publication No. 55(1980)-164356, a dry type chemical analysis slide was developed for use in a system designed for performing quantitative analyses, with which system the amount of a specific chemical constituent or a specific physical constituent contained in a droplet of a liquid sample, which is applied to the slide, is determined. It is possible to analyze a liquid sample more simply and more quickly with methods in which a chemical analysis slide is used than with methods in which a conventional wet type analysis is carried out. Therefore, it is more desirable to use chemical analysis slides, particularly in medical organizations, research laboratories, or the like, where many samples must be analyzed, than to carry out conventional wet type analyses.

In order to use a chemical analysis slide in the analysis of a chemical constituent or the like contained in a liquid sample, a measured amount of the liquid sample is put on the chemical analysis slide and is kept at a predetermined temperature (i.e. incubated) for a predetermined time in an incubator, which causes a color reaction. The chemical analysis slide is then exposed to light having a wavelength which is selected in advance, the selection of which wavelength depends on the constituents of the liquid sample and the constituents of a reagent contained in the reagent layer in the chemical analysis slide. Light is thus irradiated to a reaction product which forms on the chemical analysis slide, and the ratio of transmitted vs. reflected light is found. Thereby quantitative analysis of a chemical constituent or the like in a sample is carried out.

In medical organizations, research laboratories or the like, where many liquid samples are analyzed, it is desirable to conduct analyses automatically and sequentially. To satisfy this need, various chemical analysis apparatuses have been proposed, which use the aforesaid chemical analysis slides. One such chemical analysis apparatus is disclosed in, for example, Japanese Unexamined Patent Publication No. 56(1981)-77746. Also, as a means with which liquid samples can be automatically and sequentially analyzed, an apparatus is proposed in, for example, U.S. Pat. No. 3,526,480, in which apparatus a long tape-like test film containing a reagent is used instead of the aforesaid chemical analysis slides, and the application, incubation and measurement of samples are carried out sequentially on adjacent portions of the test film. The operating cost of an apparatus using a long tape-like test film is lower than the operating cost of an apparatus using chemical analysis slides, and a simple mechanism makes it possible for measurements to be carried out sequentially on many liquid samples.

The long test film may be housed in a film feed cassette by being wound around a feed reel and then loaded into the biochemical analysis apparatus. The film feed cassette is provided with a film outlet. The long test film is affected by temperature or humidity and will deteriorate (i.e. the chemical properties of the long test film will change) if the temperature and humidity are not closely controlled. In order to eliminate this problem, the biochemical analysis apparatus may be provided with a refrigerator which is kept at a low temperature and low humidity. A long test film is housed in the film feed cassette and then accommodated in the refrigerator so that it does not deteriorate even if a long time occurs between when it is loaded into the apparatus and when analysis begins. Also, the film feed cassette contains a desiccant, and the space inside the film feed cassette is kept in a dry state (at humidity of 0%) before the film feed cassette is loaded into the refrigerator. The refrigerator is provided with a cassette accommodating section which is enclosed by a refrigerator wall and in which the film feed cassette is accommodated releasably. Additionally, the refrigerator has a film outlet at a position corresponding to the position of the film outlet of the film feed cassette which has been loaded into the refrigerator. Therefore, after the film feed cassette has been loaded into the refrigerator, the long test film can be repeatedly pulled out through the film outlet of the film feed cassette and the film outlet of the refrigerator. When the long test film is to be used to analyze a plurality of liquid samples sequentially, portions of the long test film having a length equal to the minimum length necessary for a single analysis are pulled out sequentially. The long test film is forwarded just before each liquid sample is applied thereto.

Before the film feed cassette is loaded into the refrigerator, the film outlet thereof is closed in order to seal off the region inside of the film feed cassette completely. However, after the film feed cassette is loaded into the refrigerator, the film outlet of the film feed cassette is kept open. Therefore, a problem arises in that wet ambient air enters the film feed cassette through the film outlet of the refrigerator and the film outlet of the film feed cassette and causes the humidity inside the film feed cassette to increase. In order for the long test film in the refrigerator not to deteriorate, it is necessary for the region inside of the film feed cassette to be kept substantially dry (i.e. at a humidity of 0%). However, with conventional refrigerators, because wet ambient air enters the film feed cassette through its film outlet, the long test film may deteriorate within a period as short as several days. In order for wet ambient air to be prevented from entering the film feed cassette through the film outlet of the refrigerator and the film outlet of the film feed cassette, it has been suggested that a very dry air stream (having a humidity of approximately 0%) be introduced into the film feed cassette located in the refrigerator, and that such air should be made to jet from the film outlet of the film feed cassette. However, a device for generating very dry air has a high manufacturing cost.

SUMMARY OF THE INVENTION

The primary object of the present invention is to provide a refrigerator wherein the region inside of a film feed cassette is kept dry for a long period with a comparatively cheap means.

Another object of the present invention is to provide a novel dry air generating device wherein two air drying chambers are alternately operated, which allows dry air to be generated approximately continuously, air in an air drying chamber in which a desiccant is being regenerated can be replaced with fresh air, when necessary, and wet air does not enter a dry air feed-out path even for an instant.

The specific object of the present invention is to provide a method for operating the novel dry air generating device.

The present invention provides a refrigerator comprising a cassette accommodating section which is enclosed by a wall, kept at a low temperature, and capable of accommodating a film feed cassette such that it can be released therefrom, said film feed cassette housing therein a long test film containing a reagent which will react with a liquid sample and give rise to a change in optical density and having a film outlet through which the long test film is fed out, the refrigerator being provided with a film outlet which is formed at the position in the wall corresponding to the position of the film outlet of the film feed cassette when it is located in the cassette accommodating section, said long test film being pulled out through said film outlet of said film feed cassette, wherein the improvement comprises the provision of an air stream jetting means which generates a dry air stream between said film outlet of said film feed cassette, which film feed cassette is located in said cassette accommodating section, and said film outlet of said refrigerator so that the dry air stream is jetted to the surface of the portion of said long test film which is positioned on the side outward from and in the vicinity of said film outlet of said film feed cassette.

The term "dry air" as used herein means air whose moisture content is such that it does not cause any problem when it is being jetted to a long test film and such that with it the region inside of the film feed cassette can be kept dry for a long period. The exact moisture content of the dry air depends on the characteristics of the long test film being used. In general, the term "dry air" means air whose humidity falls within the range of approximately 10% to approximately 20%. The temperature of the dry air stream should preferably be not higher than the temperature of the refrigerator.

When a dry air stream is jetted to the surface of the portion of a long test film positioned on the side outward from and in the vicinity of the film outlet of a film feed cassette which is located in the cassette accommodating section, dry air flows out of the refrigerator through the film outlet thereof. Therefore, wet air around the refrigerator is prevented from entering the film feed cassette. As a result, the region inside of the film feed cassette is kept dry for a long period. Also, because the dry air stream can be generated with a device which is markedly cheaper than a device designed to generate completely dry air, the manufacturing cost of the refrigerator can be kept low.

The present invention also provides a dry air generating device which comprises:

(i) two air drying chambers,
(ii) heaters which independently heat and dry desiccants accommodated in two said air drying chambers,
(iii) an air feed-in valve which switches an air feed-in path so that air introduced through an air feed-in pipe is fed into either one of two said air drying chambers,
(iv) two wet air discharging valves which control the discharge of wet air from two said air drying chambers,
(v) two dry air feed-out valves which control the feeding of dry air out of two said air drying chambers, and
(vi) an air feed-out path through which both dry air streams coming from two said dry air feed-out valves are fed out.

The present invention further provides a method for operating the dry air generating device, which comprises the steps of:

(1) carrying out a normal operation wherein dry air is continuously generated with a first air drying chamber while the desiccant accommodated in a second air drying chamber is being heated by the corresponding heater in order to release moisture from the desiccant, dry air being continuously generated with said first air drying chamber with an operation in which:

(a) air introduced through said air feed-in pipe is fed into said first air drying chamber,
(b) dry air generated in said first air drying chamber is fed out through a first dry air feed-out valve corresponding to said first air drying chamber,
(c) dry air fed out through said first dry air feed-out valve is prevented by a second dry air feed-out valve corresponding to said second air drying chamber from flowing into said second air drying chamber, and
(d) dry air generated in said first air drying chamber is prevented by a first wet air discharging valve corresponding to said first air drying chamber from flowing out through said first wet air discharging valve, and (2) in the course of said normal operation being carried out, controlling the respective valves so that:

(e) air introduced through said air feed-in pipe is fed into said second air drying chamber in order to discharge air from said second air drying chamber through a second wet air discharging valve corresponding to said second air drying chamber,
(f) after air has thus been discharged from said second air drying chamber, air introduced through said air feed-in pipe is fed into said first air drying chamber, and dry air generated in said first air drying chamber is discharged through said first dry air feed-out valve, said second dry air feed-out valve, and said second wet air discharging valve, and
(g) thereafter said normal operation is restarted.

Neither the term "first air drying chamber" nor the term "second air drying chamber" as used herein means a specific one of the two air drying chambers. An arbitrary one of the two air drying chambers is referred to as the first air drying chamber, and the other air drying chamber is referred to as the second air drying chamber. Therefore, the term "regular operation" as used herein embraces both of a mode wherein dry air is generated in one of the two air drying chambers and a mode wherein dry air is generated in the other air drying chamber.

Also, the term "valve" as used herein means one of various known types of valves, such as solenoid valves and air-actuated valves.

With the dry air generating device and the method for operating it in accordance with the present invention, dry air can be continuously generated with the first air drying chamber, and simultaneously the desiccant accommodated in the second air drying chamber can be regenerated by being heated with a heater in order to cause moisture to be released from the desiccant. The dry air generating device operates in two modes: one in which dry air is generated with the first air drying chamber while the desiccant accommodated in the second air drying chamber is being regenerated and one in which dry air is generated with the second air drying chamber while the desiccant accommodated in the first air drying chamber is being regenerated. Repeatedly alternating between the modes allows dry air to be generated approximately continuously. Also, the dry air generating device in accordance with the present invention is provided with wet air discharging valves which are independent of the valves located in the dry air feed-out paths and through which wet air, which is generated when the desiccants accommodated in the two air drying chambers are regenerated, is discharged from the two air drying chambers. Therefore, air introduced through the air feed-in pipe can be fed into an air drying chamber, in which a desiccant is being regenerated, in order to discharge wet air from said air drying chamber through the corresponding wet air discharging valve, which is located in a path different from the paths through which dry air is fed out. Additionally, the dry air generating device in accordance with the present invention is provided with an air feed-out path through which both dry air streams coming from the two dry air feed-out valves are fed out. Accordingly, dry air fed out of an air drying chamber in which dry air is being generated can be discharged through the two dry air feed-out valves and the wet air discharging valve of the air drying chamber in which the desiccant is being regenerated. In this manner, it is possible to discharge even the small amount of wet air which remains at part of the path between the air drying chamber, in which the desiccant is being regenerated, and the corresponding dry air feed-out valve after the wet air has been discharged from said air drying chamber through the corresponding wet air discharging valve. Therefore, wet air does not enter the path through which dry air is fed out of the dry air generating device.

DESCRIPTION OF THE PREFERRED EMBODIMENTS

The present invention will hereinbelow be described in further detail with reference to the accompanying drawings.

Figure 1:
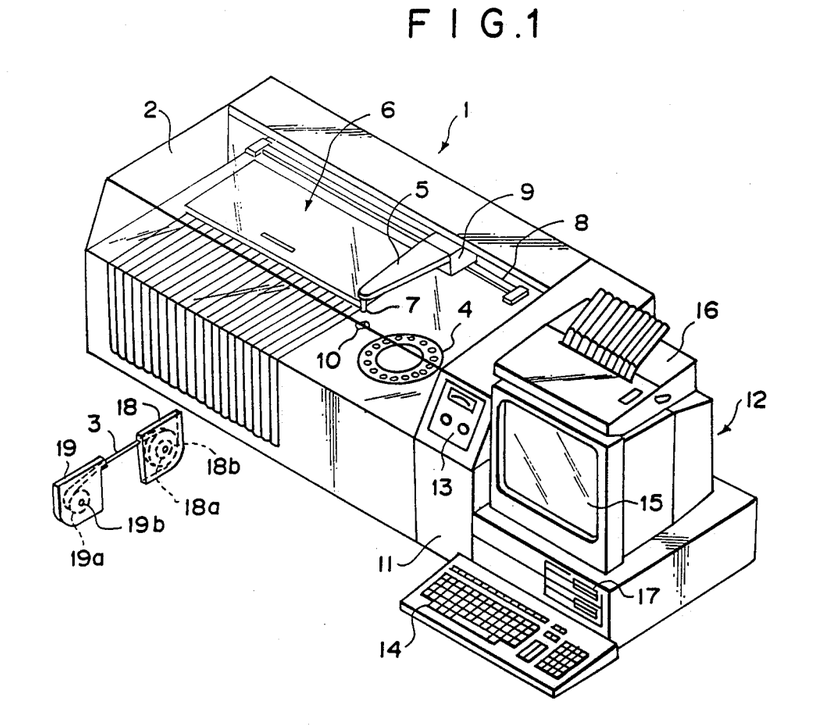
FIG. 1 is a perspective view showing a biochemical analysis apparatus wherein an embodiment of the refrigerator in accordance with the present invention is employed.

With reference to FIG. 1, a biochemical analysis apparatus 1 is provided with a transparent cover 2. The cover 2 is opened when a liquid sample, a long tape-like test film 3 and the like are fed into and out of the apparatus 1. The apparatus 1 is provided with a sample accommodating means 4, which is a ring-like structure for accommodating liquid samples, such as blood serum or urine, and a liquid sample is taken up from the sample accommodating means 4 by a sample application means 5 as will be described later. The liquid sample is applied from the sample application means 5 onto the long test film 3. The long test film 3 contains a reagent that undergoes a color reaction only with the specific chemical constituent (or the specific physical constituent) of the liquid sample that is to be analyzed, and many kinds of long test films 3, 3, ... are prepared depending on what the specific chemical constituent to be analyzed is. The portion of the long test film 3 which has not yet been used in an analysis of a liquid sample is wound up in a film feed cassette 18, and the portion of the long test film 3 which has already been used for measurement is wound up in a film wind-up cassette 19. At the center of a reel 19a in the film wind-up cassette 19, a hole 19b is provided with which the shaft of a motor engages, which motor pulls the long test film 3 out of the film feed cassette 18 after the long test film 3 has been accommodated in the biochemical analysis apparatus 1 as will be described later. Also, at the center of a reel 18a in the film wind-up cassette 18, a hole 18b is provided with which the shaft of a motor engages, which motor rewinds the long test film 3 into the film feed cassette 18 after the long test film 3 has been pulled out of the film feed cassette 18. The long test film 3 is wound up in the film feed cassette 18 and the film wind-up cassette 19, and then accommodated in the biochemical analysis apparatus 1. As shown in FIG. 1, the film feed cassette 18 and the film wind-up cassette 19 are formed independently of each other. A test film accommodating means 6 accommodates unused portions of a plurality of long test films 3, 3, ... in parallel, which allows the apparatus 1 to be used in the simultaneous analysis of various different constituents in liquid samples.

The sample application means 5 is provided with a sample applying nozzle 7 at its end and is moved along a rail 8 by a movement means 9 placed on the rail 8. The sample applying nozzle 7 takes up the liquid sample from the sample accommodating means 4 and applies it to a portion of the long test film 3, which portion has been pulled out of the test film accommodating means 6 in a manner which will be described later. The movement means 9 also moves the sample application means 5 vertically. The sample application means 5 is kept at an upper position during the time it is being moved by the movement means 9 along the rail 8, and is moved down during the times it is taking a liquid sample out of the sample accommodating means 4 and applying a liquid sample to the long test film 3 and during the time it is being washed as will be described later.

After applying the liquid sample to the test film, the sample applying nozzle 7 is washed at a nozzle washing area 10 provided between the test film accommodating means 6 and the sample accommodating means 4. The washed sample applying nozzle 7 is then later reused in another application of a liquid sample.

The test film to which the liquid sample has already been applied is incubated by an incubator, as will be described later, and subjected to measurement by a measurement means.

Control of the operation of the overall apparatus 1, the processing of data obtained from the analysis of a liquid sample and the like are carried out by an electronic processing circuit means 11 and a computer 12 connected thereto. An operating and display means 13 on the front surface of the electronic processing circuit means 11 is provided with a power source switch for the apparatus 1, an ammeter for monitoring the amount of current consumed by the apparatus 1, and the like. The computer 12 is provided with a keyboard 14, from which instructions are given to the apparatus 1, a CRT display device 15 for displaying subsidiary information related to the instructions given to the apparatus 1, data from the analysis of a liquid sample and other items, a printer 16 for printing out data obtained from the analysis of a liquid sample, and a floppy disk drive unit 17 for accommodating a floppy disk which stores information about instructions which may be given to the apparatus 1 and data obtained from the analysis of a liquid sample.

Figure 2:
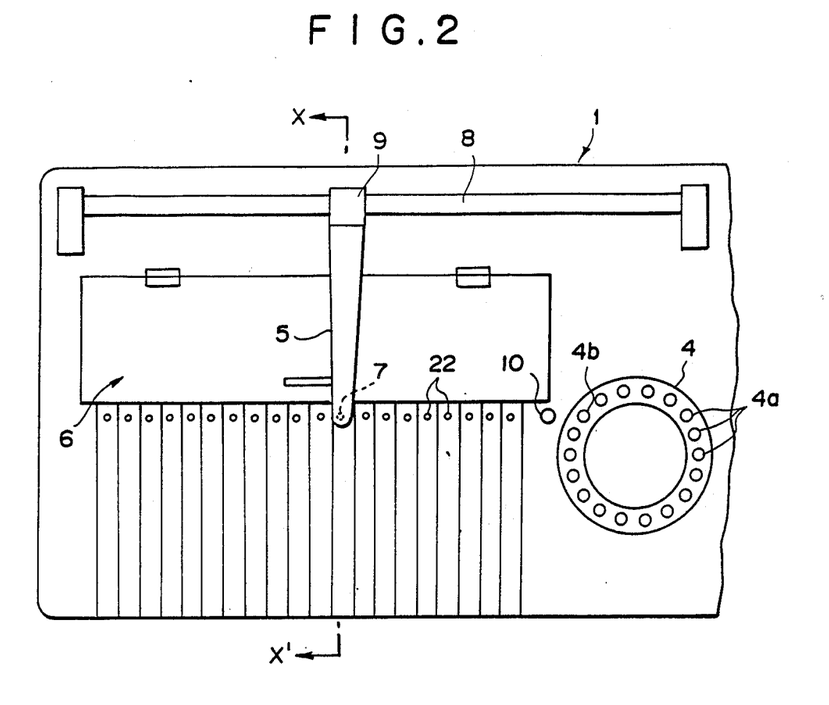
FIG. 2 is a plan view showing the major part of the biochemical analysis apparatus shown in FIG. 1.

With reference to FIG. 2, which shows a major part of the apparatus 1, the test film accommodating means 6 is constituted so that an imaginary line connecting the sample applying positions 22, 22, . . . for all of the long test films 3, 3, . . . is straight. Also, the nozzle washing area 10, and a liquid sample take-out position 4b in the sample accommodating means 4 are disposed on said imaginary line.

The sample accommodating means 4 accommodates a plurality of liquid samples in accommodating regions 4a, 4a, . . . which are in the ring-like structure. The accommodating regions 4a, 4a, . . . are automatically rotated by a rotation means (not shown) until the liquid sample, which is accommodated in one of the accommodating regions 4a, 4a, . . . and is to be used in the next analysis, arrives at the take-out position 4b. In order to prevent the liquid samples accommodated in the accommodating regions 4a, 4a, . . . from evaporating and deteriorating, a cover (not shown) is provided over the accommodating regions 4a, 4a, . . . A break in the cover exists at the take-out position 4b.

The sample application means 5 is moved by the movement means 9 along the rail 8, takes up the liquid sample from the take-out position 4b, and applies it to a sample applying position 22 on the long test film.

Figure 3:
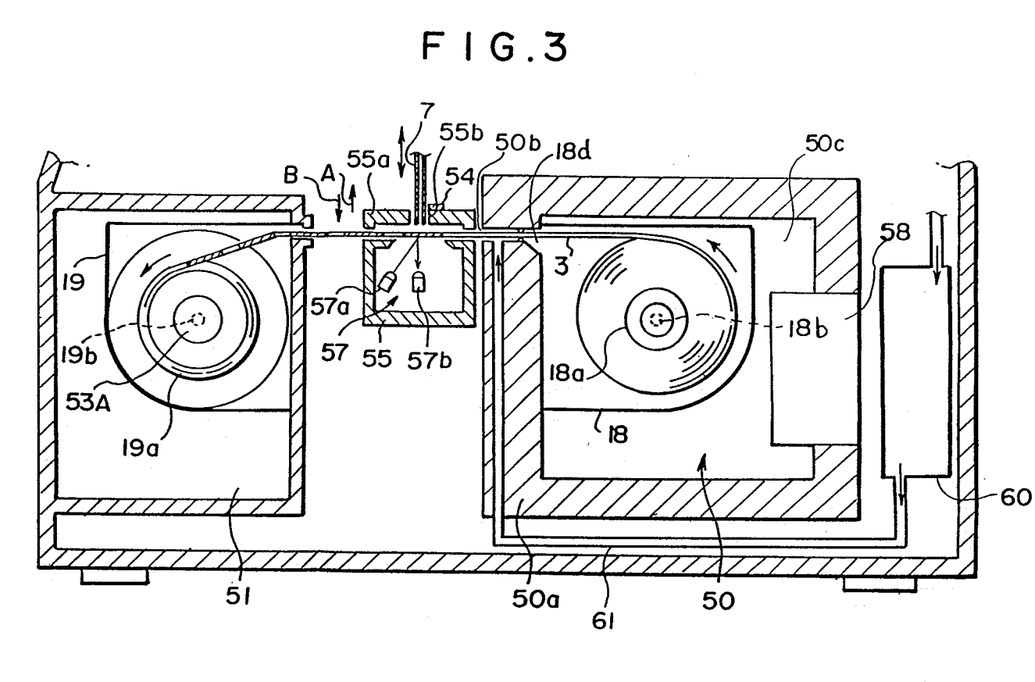
FIG. 3 is a schematic view showing the major part of the cross-sectional configuration taken along line X—X= of FIG. 2.

FIG. 3 shows the sectional configuration taken along line X—X= of FIG. 2. In FIG. 3, similar elements are numbered with the same reference numerals with respect to FIGS. 1 and 2.

With reference to FIG. 3, a long test film 3 is accommodated in the film feed cassette 18 and is fed into the apparatus 1. As portions of the long test film 3 are used in the apparatus 1, the used portions are sequentially wound up in the film wind-up cassette 19. The film feed cassette 18 is accommodated in a refrigerator 50 in which the temperature is adjusted to 15° C., by way of example, and the film wind-up cassette 19 is accommodated in a wind-up chamber 51. The refrigerator 50 has a cassette accommodating section 50c, which is enclosed by a refrigerator wall 50a composed of a heat insulating material and which accommodates the film feed cassette 18. A cooling device 58 is provided on one surface of the refrigerator wall 50a. The cooling device 58 comprises a temperature sensor and a Peltier element which is intermittently activated by a detection signal fed from the temperature sensor in order to ensure that cool air is delivered to the refrigerator and the region inside of the cassette accommodating section 50c is kept at the predetermined temperature. The cassette accommodating section 50c and the film feed cassette 18 are shaped such that they can receive and circulate cool air delivered by the Peltier element. Therefore, the temperature in the region inside of the cassette accommodating section 50c is kept approximately uniform. A fan may be located in the cassette accommodating section 50c so that the air can be circulated and the temperature in the region inside of the cassette accommodating section 50c can be kept uniform. As the temperature in the region inside of the cassette accommodating section 50c is kept low, the temperature of the film feed cassette 18 accommodated in the cassette accommodating section 50c is also kept low. Also, a desiccant (not shown in FIG. 3) is located in the film feed cassette 18, and the region inside of the film feed cassette 18 is kept dry until a film outlet 18d formed at an edge of the film feed cassette 18 is opened in order to allow the long test film 3 to be pulled out. The refrigerator 50 is provided with a film outlet 50b which is formed in the refrigerator wall 50a at a position corresponding to the position of the film outlet 18d of the film feed cassette 18 when it is located in the cassette accommodating section 50c. Portions of the long test film 3 which have been sequentially pulled out through the film outlet 18d of the film feed cassette 18 pass through the film outlet 50b of the refrigerator 50, are used in an analysis, and are wound up into the film wind-up cassette 19.

The shaft of a wind-up motor 53A, which acts as a conveyance means for the long test film 3, winds the long test film 3 around the reel 19a of the film wind-up cassette 19 by engaging the hole 19b formed at the center of the reel 19a. As the motor 53A rotates, the long test film 3 is pulled out of the film feed cassette 18 through the film outlet 50b of the refrigerator 50 and is wound up in the film wind-up cassette 19.

Because a used long test film 3 is accommodated in the film wind-up cassette 19, it can be taken out of the apparatus 1 and discarded or processed for other purposes without being touched by the operator of the apparatus 1.

An incubator 55, in which the long test film 3 incubates and through which the long test film 3 then passes, is provided between the film feed cassette 18 and the film wind-up cassette 19. A measurement means 57 is provided in the incubator 55. The measurement means 57 measures the optical density of the appropriate portion of the long test film 3. The optical density depends on how much of a reaction product was formed from the reaction between the liquid sample and the reagent in the long test film 3.

The long test film 3 is intermittently pulled out of the refrigerator 50 by the motor 53A, and intermittently fed leftward in FIG. 3. Prior to this step, an upper cover 55a of the incubator 55 is moved up in the direction indicated by the arrow A. After the long test film 3 is moved forward (to the left in FIG. 3), the upper cover 55a is moved down in the direction indicated by the arrow B. The downward action of the upper cover 55a pushes down the long test film 3. Then, a shutter 54 covering a hole 55b in the upper cover 55a, through which the sample applying nozzle 7 is to be inserted, is moved rightward, and as illustrated the sample applying nozzle 7 is moved down from above the incubator 55 to apply a liquid sample to the long test film 3 through the hole 55b. Thereafter, the sample applying nozzle 7 is moved up, and the shutter 54 is moved leftward and covers the hole 55b, which prevents air from flowing between the inside and outside of the incubator 55. Accordingly, the temperature in the incubator 55 is kept at a predetermined level, for example, 37° C. The film portion, to which the liquid sample has been applied and over which it has spread, is indicated by the hatching in FIG. 3 and is incubated for a predetermined time (four minutes, for example) in the incubator 55. In the course of the incubation or after the incubation is finished, the optical density of the portion of the long test film 3, to which the liquid sample has already been applied, is found with the measurement means 57. The density is found by a process wherein light produced by a light irradiation means 57a, which light has a wavelength which is selected in advance, is irradiated onto the long test film 3, and the light reflected by the long test film 3 is detected by use of a photodetector 57b.

Application of the next liquid sample becomes possible after the application, incubation and analysis of a previously applied liquid sample are completed in the manner described above. The long test film 3 remains inside the incubator 55 after the analysis of the most recently applied liquid sample is finished, and is moved just prior to the application of the next sample to be analyzed, which brings the film portion which is to be used for the next analysis to the sample applying position.

After the film feed cassette 18 is accommodated in the refrigerator 50, the film outlet 18d of the film feed cassette 18 is always open. Therefore, ambient air, which has a comparatively high temperature and humidity, readily enters the film feed cassette 18 through the film outlet 50b of the refrigerator 50 and the film outlet 18d of the film feed cassette 18. Therefore, even though the desiccant is accommodated in the film feed cassette 18, the humidity in the film feed cassette 18 cannot be kept low. In order to eliminate this problem, this embodiment of the refrigerator is provided with an air stream jetting means which generates a dry air stream between the film outlet 18d of the film feed cassette 18, which has been located in the cassette accommodating section 50c, and the film outlet 50b of the refrigerator 50 so that the dry air stream is jetted from below to the surface of a portion of the long test film 3 positioned on the side outward from and in the vicinity of the film outlet 18d of the film feed cassette 18. By way of example, the dry air stream is jetted in a direction approximately normal to the surface of the portion of the long test film 3. The dry air stream prevents wet ambient air from entering the film feed cassette 18.

Figure 4:
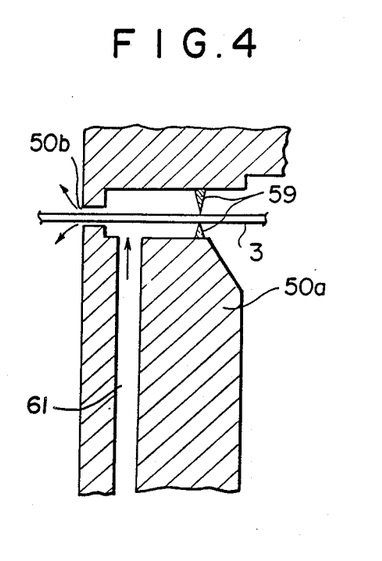
FIG. 4 is an enlarged view showing the major part of the refrigerator.

The air stream jetting means comprises a dry air generating device 60, which dries air introduced from the exterior and generates air having a humidity of, for example, approximately 10% and feeds it out, and a nozzle 61, which guides dry air fed out of the dry air generating device 60 to the vicinity of the film outlet 18d of the film feed cassette 18. As shown in FIG. 4, the refrigerator 50 is also provided with a pair of flaps 59, 59 between the outlet of the nozzle 61 and the film outlet 18d of the film feed cassette 18. The flaps 59, 59 may be constituted of silicone rubber or the like. The long test film 3 is pulled out of the refrigerator 50 via the flaps 59, 59. Before being jetted from the nozzle 61, dry air should preferably be cooled to a temperature approximately equal to the temperature of air in the cassette accommodating section 50c.

Figure 5:
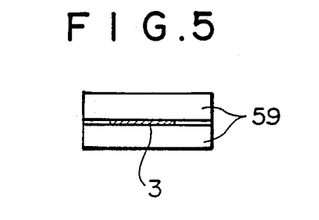
FIG. 5 is a schematic view showing blades and a long test film.

When a dry air stream is jetted from the nozzle 1, it flows to the exterior of the refrigerator 50 as illustrated in FIG. 4, and therefore wet air which may be present around the refrigerator 50 cannot enter the refrigerator 50. Therefore, air in the film feed cassette 18 is kept dry for a long period. The dry air stream jetted from the nozzle 61 need not be completely dry, but may have a humidity falling within the range of approximately 10% to approximately 20%. A dry air generating device 60 designed to generate such a dry air stream is comparatively cheap. As described above, a pair of flaps 59, 59 is located between the outlet of the nozzle 61 and the film outlet 18d of the film feed cassette 18. As shown in FIG. 5, when the long test film 3 passes between the flaps 59, 59, gaps occur between the flaps 59, 59 at both sides of the long test film 3. Part of the dry air stream jetted from the nozzle 61 will pass through the gaps into the film feed cassette 18 and slightly affect the dry air in the film feed cassette 18. Dry air jetted from the nozzle 61 contains more moisture than the dry air in the film feed cassette 18. However, experiments revealed that, with this embodiment of the refrigerator, the region inside of the film feed cassette 18 can be kept in a desirable dry state for approximately one month.

If wet air enters the dry air stream, which is jetted from the nozzle 61, even for an instant, part of the wet air will pass through the gaps on both sides of the long test film 3 between the flaps 59, 59, and enter the refrigerator 50. Such wet air quickly causes the long test film 3 to deteriorate in the vicinity of the flaps 59, 59. Therefore, the dry air stream jetted from the nozzle 61 must always be kept in the desired dry state. In cases where there is the risk of wet air being jetted from the nozzle 61 even for an instant, the jetting of the dry air stream should be stopped for a short time.

Also, as described above, air in the region inside of the film feed cassette 18 is more dry than the dry air generated by the dry air generating device 60. Therefore, dry air generated by the dry air generating device 60 is not directly jetted into the refrigerator 50, but is jetted to the vicinity of the film outlet 50b of the refrigerator 50. In this manner, wet ambient air is prevented from entering the film feed cassette 18, and the region inside of the film feed cassette 18 is kept substantially dry by the desiccant for a long period.

Figure 6:
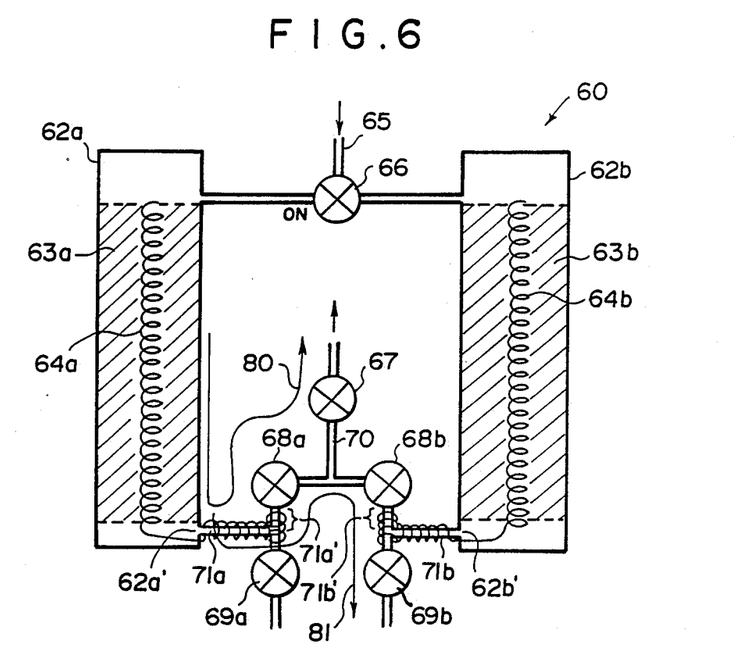
FIG. 6 is a schematic view showing an embodiment of the dry air generating device in accordance with the present invention.
Figure 7:
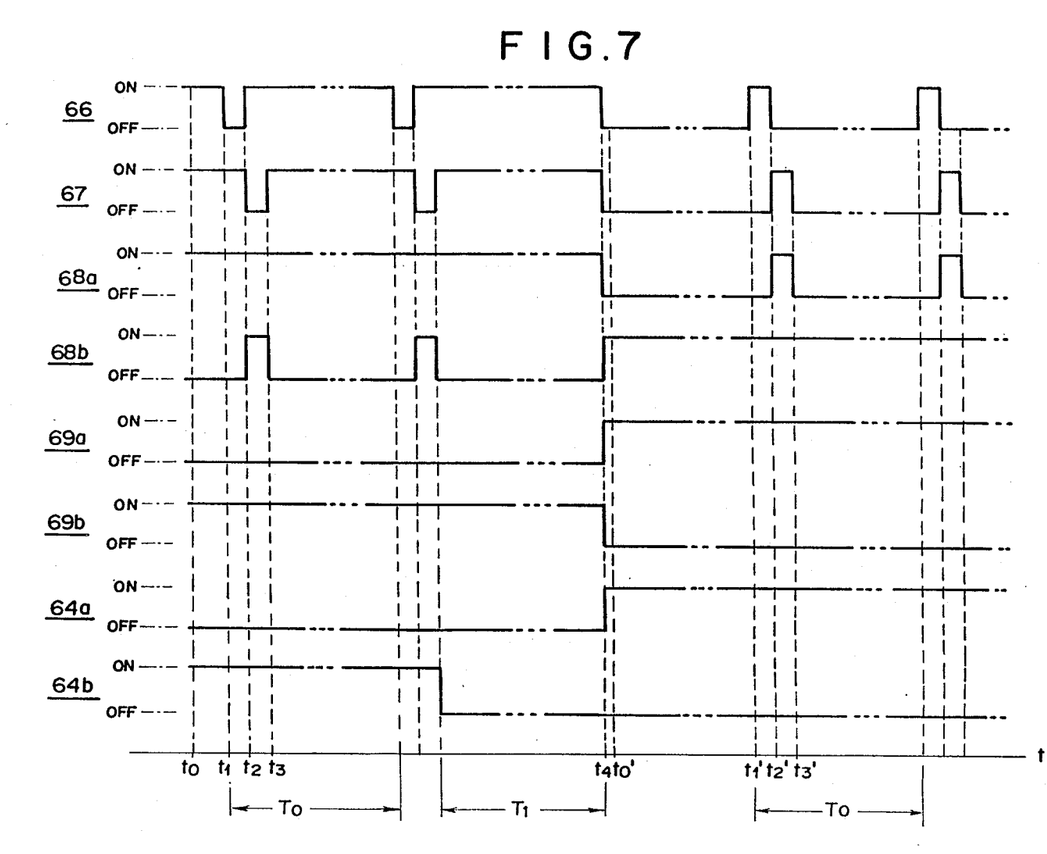
FIG. 7 is a timing chart showing the relative operating times of the solenoid valves and heaters in the embodiment of the dry air generating device shown in FIG. 6.

FIG. 6 shows the configuration of the dry air generating device 60 shown in FIG. 3, and FIG. 7 is a timing chart showing the relative operating times of the solenoid valves and heaters in the dry air generating device 60 shown in FIG. 6.

The dry air generating device 60 comprises air drying chambers 62a and 62b, heaters 64a and 64b which independently heat and dry desiccants 63a and 63b respectively accommodated in the air drying chambers 62a and 62b, and an air feed-in solenoid valve 66 which switches an air feed-in path such that air introduced through an air feed-in pipe 65 from an air feed-in pump (not shown) is fed into either one of the air drying chambers 62a and 62b. (When the air feed-in solenoid valve 66 is on, air is fed into the first air drying chamber 62a which is located on the left side in FIG. 6. The configuration of the dry air generating device 60 is symmetric in FIG. 6, and therefore the left one of two elements symmetrically located with respect to each other will hereinafter be referred to as the first element, and the right one will be referred to as the second element.) The dry air generating device 60 also comprises a first wet air discharging solenoid valve 69a and a second wet air discharging solenoid valve 69b which respectively control the discharge of wet air from the first air drying chamber 62a and the second air drying chamber 62b. The dry air generating device 60 is further provided with a first dry air feed-out solenoid valve 68a and a second dry air feed-out solenoid valve 68b which respectively control the feeding of dry air out of the first air drying chamber 62a and the second air drying chamber 62b, and an air feed-out path 70 through which both dry air streams coming from the first dry air feed-out solenoid valve 68a and the second dry air feed-out solenoid valve 68b are fed out. Additionally, a common air feed-out solenoid valve 67 is provided and controls the feeding of dry air through the air feed-out path 70. Dry air fed through the common air feed-out solenoid valve 67 is guided by the nozzle 61 to the vicinity of the film outlet 50b of the refrigerator 50 as illustrated in FIG. 3.

As shown in FIG. 6, in this embodiment, the first air drying chamber 62a has a single air outlet 62a=, and the second air drying chamber 62b has a single air outlet 62b=. The air outlet 62a= is connected to an air flow-out pipe 71a which forks into two branches, which are respectively connected to the first dry air feed-out solenoid valve 68a and the first wet air discharging solenoid valve 69a. Also, air outlet 62b= is connected to an air flow-out pipe 71b which forks into two branches, which are respectively connected to the second dry air feed-out solenoid valve 68b and the second wet air discharging solenoid valve 69b. As shown in FIG. 6, in this embodiment, the heater 64a also heats air in the air flow-out pipe 71a extending from the air outlet 62a= to the first dry air feed-out solenoid valve 68a and the first wet air discharging solenoid valve 69a. The heater 64b also heats air in the air flow-out pipe 71b extending from the air outlet 62b= to the second dry air feed-out solenoid valve 68b and the second wet air discharging solenoid valve 69b. Accordingly, moisture released from the desiccants 63a and 63b when they are heated by the heaters 64a and 64b can be reliably prevented from being cooled and forming water droplets in the air flow-out pipes 71a and 71b.

Solenoid valves are used in this embodiment. However, the valves in the dry air generating device in accordance with the present invention are not limited to solenoid valves, and may be any other known valves, such as air-actuated valves.

How the dry air generating device 60 operates will be described hereinbelow.

With reference to FIG. 7, time is plotted on the horizontal axis t. At time t0, a normal operation is being carried out wherein dry air is generated with the first air drying chamber 62a while the heater 64b is heating and regenerating the desiccant 63b in the second air drying chamber 62b. As described above, when the air feed-in solenoid valve 66 is on, air is fed into the first air drying chamber 62a. When the air feed-in solenoid valve 66 is off, air is fed into the second air drying chamber 62b. As for the common air feed out solenoid valve 67, the first dry air feed-out solenoid valve 68a, the second dry air feed-out solenoid valve 68b, the first wet air discharging solenoid valve 69a, and the second wet air discharging solenoid valve 69b, air passes therethrough when they are on and does not pass therethrough when they are off.

During normal operation (i.e. at time t0), the air feed-in solenoid valve 66 is on, and therefore air introduced through the air feed-in pipe 65 flows into the first air drying chamber 62a. Also, the first dry air feed-out solenoid valve 68a and the common air feed-out solenoid valve 67 are on, and the second dry air feed-out solenoid valve 68b and the first wet air discharging solenoid valve 69a are off. Therefore, air fed into the first air drying chamber 62a passes through gaps in the desiccant 63a and is desiccated thereby, and the dry air thus generated flows out along a route 80 as shown in FIG. 6. On the other hand, the heater 64b in the second air drying chamber 62b is on and heats the desiccant 63b which has already absorbed much moisture and therefore has a low desiccating capacity. The heater 64b causes moisture to evaporate from the desiccant 63b and therefore regenerates it. In this embodiment, during normal operation, the second wet air discharging solenoid valve 69b is on. Because no air is fed through the air feed-in valve 66 into the second air drying chamber 62b during normal operation, air present in the second air drying chamber 62b is not replaced with fresh air. Therefore, the second wet air discharging solenoid valve 69b may be turned off during normal operation and turned on when necessary, for example, when wet air is to be discharged from the second air drying chamber 62b.

The normal operation is periodically interrupted so that the operation described below may be carried out. The operation described below is carried out in order to discharge the wet air which appears in the second air drying chamber 62b when the desiccant 63b is heated and moisture evaporates therefrom.

First, at time t1, the air feed-in solenoid valve 66 is turned off, and air introduced through the air feed-in pipe 65 is fed into the second air drying chamber 62b. As a result, wet air is discharged from the second air drying chamber 62b through the second wet air discharging solenoid valve 69b.

However, when wet air is discharged from the second air drying chamber 62b through the second wet air discharging solenoid valve 69b, wet air which is present at a part 71b= of the air flow-out pipe 71b is not discharged. Therefore, at time t2, the air feed-in solenoid valve 66 is turned on, and air introduced through the air feed-in pipe 65 is fed into the first air drying chamber 62a. Also, the common air feed-out solenoid valve 67 is turned off, and the second dry air feed-out solenoid valve 68b is turned on. As a result, dry air generated in the first air drying chamber 62a flows along a route 81 as shown in FIG. 6 and causes the wet air in part 71b= to be discharged through the second wet air discharging solenoid valve 69b. In this embodiment, the common air feed-out solenoid valve 67 is turned off. Alternatively, the common air feed-out solenoid valve 67 may be kept on, so that dry air generated in the first air drying chamber 62a is fed out along the route 80 and is simultaneously discharged along the route 81. Therefore, the common air feed-out solenoid valve 67 need not necessarily be provided. In this manner, all the wet air is discharged from the second air drying chamber 62b and the air flow-out pipe 71b. Accordingly, wet air is prevented from entering the dry air feed-out path even for an instant at time t4 at which normal operation shifts to a mode wherein dry air is generated with the second air drying chamber 62b.

After all the wet air has been discharged from the second air drying chamber 62b and the air flow-out pipe 71b, normal operation (i.e. the same operation as that at time t0) is restarted.

The operations described above are repeated with a predetermined period T0. After the desiccant 63b has been regenerated, the heater 64b turns off, and air in the second air drying chamber 62b is allowed to cool naturally (for a period T1 shown in FIG. 7). The period T0 need not necessarily be constant. For example, the operation for discharging wet air from the second air drying chamber 62b may be carried out each time the humidity of air in the second air drying chamber 62b has increased to a predetermined level. When air in the second air drying chamber 62b is allowed to cool naturally, the air in the second air drying chamber 62b and the air flow-out pipe 71b is dry. At time t4, after the air in the second air drying chamber 62b has cooled substantially, the respective solenoid valves are switched in order to allow dry air to be generated with the second air drying chamber 62b and the desiccant 63a in the first air drying chamber 62a to be regenerated. As described above, the configuration of the dry air generating device 60 shown in FIG. 6 is symmetric. Therefore, at and after time t4, the respective solenoid valves and heaters are operated in the same manner as described above for the corresponding symmetrically located ones. Therefore, an explanation about the mode wherein dry air is generated with the second air drying chamber 62b is omitted.

With the dry air generating device 60, dry air can be generated and fed out nearly continuously, except for a short time during which the feeding of dry air through the air feed-out path 70 is interrupted in order to allow wet air to be discharged from the device. Therefore, in the biochemical analysis apparatus 1 shown in FIG. 1 wherein the dry air generating device 60 is employed, the unused long test film 3 accommodated in the film feed cassette 18 can be kept substantially dry for a long period.

We claim:

1. A refrigerator comprising a cassette accommodating section which is enclosed by a wall, kept at a low temperature, and capable of accommodating a film feed cassette such that it can be released therefrom, said film feed cassette housing therein a long test film containing a reagent which will react with a liquid sample and give rise to a change in optical density and having a film outlet through which the long test film is fed out, the refrigerator being provided with a film outlet which is formed at the position in the wall corresponding to the position of the film outlet of the film feed cassette when it is located in the cassette accommodating section, said long test film being pulled out through said film outlet of said film feed cassette, wherein the improvement comprises the provision of an air stream jetting means for generating a dry air stream between said film outlet of said film feed cassette, which film feed cassette is located in said cassette accommodating section, and said film outlet of said refrigerator so that the dry air stream is jetted to the surface of the portion of said long test film which is positioned on the side outward from and in the vicinity of said film outlet of said film feed cassette.

2. A refrigerator as defined in claim 1 wherein said air stream jetting means jets a dry air stream in a direction approximately normal to the surface of the portion of said long test film positioned on the side outward from and in the vicinity of said film outlet of said film feed cassette which has been located in said cassette accommodating section.

3. A refrigerator as defined in claim 1 wherein the temperature of the dry air stream jetted to the surface of the portion of said long test film positioned on the side outward from and in the vicinity of said film outlet of said film feed cassette which has been located in said cassette accommodating section is not higher than the temperature of said refrigerator.

4. A refrigerator as defined in claim 1 wherein a pair of flaps is located between said film outlet of said film feed cassette which has been located in said cassette accommodating section and the position at which the jetted dry air stream impinges upon the surface of the portion of said long test film positioned on the side outward from and in the vicinity of said film outlet of said film feed cassette, so that said long test film passes between said flaps.

5. A refrigerator as defined in claim 1 wherein said air stream jetting means is provided with a dry air generating device which comprises:
   (i) two air drying chambers,
   (ii) heaters which independently heat and dry desiccants accommodated in two said air drying chambers,
   (iii) an air feed-in valve which switches an air feed-in path so that air introduced through an air feed-in pipe is fed into either one of two said air drying chambers,
   (iv) two wet air discharging valves which control the discharge of wet air from two said air drying chambers,
   (v) two dry air feed-out valves which control the feeding of dry air out of two said air drying chambers, and
   (vi) an air feed-out path through which both dry air streams coming from two said dry air feed-out valves are fed out.

6. A refrigerator as defined in claim 5 wherein said heaters also heat air in an air flow-out pipe extending from an air outlet of a first air drying chamber to a first dry air feed-out valve and a first wet air discharging valve, and air in an air flow-out pipe extending from an air outlet of a second air drying chamber to a second dry air feed-out valve and a second wet air discharging valve.

7. A refrigerator as defined in claim 5 wherein said dry air generating device is operated with a method which comprises the steps of:
   (1) carrying out a normal operation wherein dry air is continuously generated with a first air drying chamber while the desiccant accommodated in a second air drying chamber is being heated by the corresponding heater in order to release moisture from the desiccant, dry air being continuously generated with said first air drying chamber with an operation in which:
      (a) air introduced through said air feed-in pipe is fed into said first air drying chamber,
      (b) dry air generated in said first air drying chamber is fed out through a first dry air feed-out valve corresponding to said first air drying chamber,
      (c) dry air fed out through said first dry air feed-out valve is prevented by a second dry air feed-out valve corresponding to said second air drying chamber from flowing into said second air drying chamber, and (d) dry air generated in said first air drying chamber is prevented by a first wet air discharging valve corresponding to said first air drying chamber from flowing out through said first wet air discharging valve, and (2) in the course of said normal operation being carried out, controlling the respective valves so that:

(e) air introduced through said air feed-in pipe is fed into said second air drying chamber in order to discharge air from said second air drying chamber through a second wet air discharging valve corresponding to said second air drying chamber, (f) after air has thus been discharged from said second air drying chamber, air introduced through said air feed-in pipe is fed into said first air drying chamber, and dry air generated in said first air drying chamber is discharged through said first dry air feed-out valve, said second dry air feed-out valve, and said second wet air discharging valve, and (g) thereafter said normal operation is restarted.

* * * * *